United States Patent [19]
Sole et al.

[11] Patent Number: 6,080,788
[45] Date of Patent: Jun. 27, 2000

[54] COMPOSITION FOR IMPROVEMENT OF CELLULAR NUTRITION AND MITOCHONDRIAL ENERGETICS

[76] Inventors: Michael J. Sole, 706 Briar Hill Ave., Toronto, Ontario, Canada, M6B 1L3; Khursheed N. Jeejeebhoy, 69 Boulton Dr., Toronto, Ontario, Canada, M4V 2V5

[21] Appl. No.: 09/002,765

[22] Filed: Jan. 6, 1998

Related U.S. Application Data

[63] Continuation-in-part of application No. 08/826,234, Mar. 27, 1997, abandoned.

[51] Int. Cl.$^7$ ................................................... A61K 31/555
[52] U.S. Cl. ........................ 514/561; 514/718; 514/665; 514/904
[58] Field of Search ...................... 514/904, 561, 514/718, 665

[56] References Cited

U.S. PATENT DOCUMENTS

| | | | |
|---|---|---|---|
| 3,974,087 | 8/1976 | Wan et al. | 260/396 R |
| 4,599,232 | 7/1986 | Bertelli . | |
| 4,687,782 | 8/1987 | Brantman et al. | 514/561 |
| 4,920,098 | 4/1990 | Cotter et al. | 514/2 |
| 5,260,464 | 11/1993 | Valle et al. | 554/80 |
| 5,270,297 | 12/1993 | Paul et al. | 514/23 |
| 5,582,839 | 12/1996 | McCarty | 424/489 |
| 5,654,011 | 8/1997 | Jackson et al. | 424/635 |

FOREIGN PATENT DOCUMENTS

| | | | |
|---|---|---|---|
| 0659349 | 12/1984 | European Pat. Off. . | |
| 0129418 | 7/1986 | European Pat. Off. . | |
| 354848A1 | 2/1990 | European Pat. Off. | A61K 31/205 |
| 452210A1 | 10/1991 | European Pat. Off. | A61K 31/205 |
| 561745A2 | 9/1993 | European Pat. Off. | A23L 1/03 |
| 680945A2 | 11/1995 | European Pat. Off. | C07C 229/22 |
| 697397A1 | 2/1996 | European Pat. Off. | C07C 229/22 |
| 03094655 | 4/1991 | Japan . | |
| 7330584 | 12/1995 | Japan | A61K 9/08 |
| 2230418 | 10/1990 | United Kingdom . | |
| 8901740 | 3/1989 | WIPO . | |
| 9215546 | 2/1992 | WIPO | C07C 62/00 |
| 9402127 | 2/1994 | WIPO | A61K 31/195 |
| 9414458 | 7/1994 | WIPO . | |
| 9529684 | 11/1995 | WIPO | A61K 33/04 |
| 9618313 | 6/1996 | WIPO | A23L 1/305 |
| 9738685 | 10/1997 | WIPO | A61K 31/195 |

*Primary Examiner*—Keith D. MacMillan
*Attorney, Agent, or Firm*—Nields, Lemack & Dingman

[57] ABSTRACT

This invention provides a dietary supplement comprising L-Carnitine (or its functional analogues such as Acetyl-Carnitine or Proprionyl-l-Carnitine), Coenzyme Q10 and Taurine for the correction of the abnormality in mitochondrial energetics in cardiac failure and certain other diseases. A high protein nutritional feeding supplementation with Cysteine, Creatine, Vitamin E (RRR-d-alpha-tocopherol), Vitamin C (ascorbic acid), Selenium, and Thiamin in may be added.

25 Claims, 7 Drawing Sheets

CONTROL NON-TREATED HEART

C. NORMAL HAMSTER HEART

A. CONTROL NON-TREATED HEART

B. COCKTAIL TREATED HEART

B. COCKTAIL TREATED HEART

COMPOSITION FOR IMPROVEMENT OF CELLULAR NUTRITION AND MITOCHONDRIAL ENERGETICS

CROSS REFERENCE TO RELATED APPLICATION

This application is a continuation-in-part of U.S. application Ser. No. 08/826,234 filed Mar. 27, 1997, entitled Nutritional Composition for Improvement of Cell Energetics abandoned.

BACKGROUND

This Application

This application is a continuation-in-part of application Ser. No. 08/826,234 filed Mar. 27, 1997, entitled Nutritional Composition for Improvement of Cell Energetics abandoned.

Organ Failure and Nutrition

There are four critical organ systems that are especially likely to fail in aging and critical illness. They are the cardiovascular, central nervous, musculoskeletal and immune systems. We have found that nutrition can be used to prevent or delay the onset of cardiac failure and thereby, promote recovery in disease states affecting the heart. Similar considerations apply to diseases of the other organ systems indicated above.

We have found that the central effect of nutrition in all these systems can be unified into its influence on mitochondrial energetics. That is: inadequate nutitional substrate is a cause of impaired cell energetics. This has led us to invent a composition for the improvement of mitochondrial energetics.

Relationship of malnutrition to mitochondrial function.

Protein-calorie malnutrition contributes to both skeletal and cardiac[1] muscle dysfunction in patients with cardiac failure. Muscle is composed of water, minerals, nitrogen and glycogen[2,3]. Feeding wasted individuals results in a gain of the multiple elements in lean tissue[4] including potassium. Body potassium, has been used as an index of body cell mass[5], the metabolically active component of the lean tissue. In contrast to body nitrogen, body potassium responds rapidly to feeding by both oral and intravenous routes[6,7,8,9,10]. It has been shown that in malnutrition there is a change in muscle membrane potential resulting in reduced intracellular ionic potassium. The reduced cellular potassium cannot be simply corrected by giving potassium but requires restitution of nutrition. The above mentioned observations suggest that cell ion uptake, an energy dependent process, occurs earlier than protein synthesis during nutritional support. This concept has received experimental support by two studies using $^{31}$P-NMR which showed that malnutrition was associated with a reduced rate of oxidative phosphorylation, suggesting a mitochondrial abnormality[11,12].

Cell energetics are also important for muscle activity and it has been shown[13,14,15,16,17,18,19,20,21,22] that skeletal muscle function, including that of the diaphragm, can be rapidly altered by nutrient deprivation and restored by refeeding. Also the changes in muscle function are specific to alterations in the nutritional status and are not influenced by sepsis, trauma, renal failure and steroid administration[15,17]. Christie and Hill indicated that nutritional support improves muscle, including diaphragmatic function before any increase in body protein or body mass[20]. Windsor and Hill[21] demonstrated that the functional effects of nutrition are more important than subnormal body protein as an index of surgical risk. Hanning and her colleagues[22] demonstrated the ability of stimulated muscle function as demonstrated by a slow relaxation rate and an altered force-frequency curve to predict the ability of patients with cystic fibrosis to grow as an outcome measure. In contrast, body composition, protein biochemistry, muscle power on an ergometer or use of supplements did not predict growth potential. Among the macronutrients, Castenada et al[23] have shown that protein deficiency can profoundly alter muscle function even when energy intake is sufficient to meet requirements.

The data given above indicate that it is critical to correct protein-calorie malnutrition, with an emphasis on protein repletion, in order to obtain the maximum functional benefits of administering cardiac specific micronutrients. Current diet supplementing strategies for correcting protein-calorie malnutrition focus on giving supplements of protein and energy (carbohydrates and fats). No supplement to date has addressed the cascading series of metabolic abnormalities that can lead to mitochondrial dysfunction. We have shown that in the skeletal muscle protein-calorie malnutrition profoundly reduces mitochondrial oxidative phosphorylation and reduces calcium cycling in cardiac muscle[1].

We have found that there is profound reduction of respiratory chain complex I, II and IV activity in animals given a protein-calorie deficient diet. In addition, complex I activity is similarly reduced in lymphocyte mitochondria showing that these effects are not cardiac specific but apply to mitochondria in other tissues, and protein feeding rapidly restored the abnormality when it was simply due to protein-energy malnutrition (unpublished data).

In addition, certain micronutrients and amino acids also influence mitochondrial function in general. For example, camitine improves mitochondrial DNA transcription and translation in aged animals[24]. A specific acyl derivative of carnitine, acetyl-carnitine has been used for mitochondrial DNA synthesis based on findings observed in patients treated with anti-retroviral agents[25]. Coenzyme Q can alter immune function[26] and may protect the central nervous system from injury and neurodegeneration[21]. On the basis of the above considerations, a nutritional supplement that could maintain or restore mitochondrial function will prevent cardiac failure or aid recovery from cardiac disease. In addition it could also aid in the management of neurodegenerative, musculoskeletal including the muscular abnormality in chronic obstructive lung disease (COPD)[16] and immune disorders.

Heart Failure.

Congestive heart failure has emerged as a major health problem during the past two decades. Its morbidity and mortality have shown a steady increase since 1970[28]; heart failure now affects approximately 1% of the population of the United States and Canada. These data reflect both the aging of our population and the success of modern cardiovascular medicine in converting acute, often previously fatal, cardiac disease into a more chronic process.

The underlying abnormality in congestive heart disease is myocardial dysfunction leading to inadequate blood flow to peripheral tissues. Although there have been considerable advances in our understanding of the pathogenesis of heart failure in recent years, critical questions remain about the evolution of cardiac dysfunction to terminal failure. The importance of elucidating the mechanisms responsible for the evolution of maladaptive hypertrophy to cardiac failure is emphasized by the fact that in spite of our advances, no presently available therapeutic intervention has been shown to substantially improve the long-term survival of patients with dilated cardiomyopathy and congestive heart failure. The underlying heart disease is relentlessly progressive in almost all patients who develop symptoms of overt failure and mortality continues to be unacceptably high; for example, in a recent heart failure trial, SOLVD, 40% of patients in the symptomatic treated group were dead within 4 years[29]. Heart transplantation appears to be the only prospect to improve long term survival for many patients.

The reason for this dismal outcome despite modern advances lies in the fact that several metabolic abnormalities have been found in the failing myocardium which together as indicated below result in progressive loss of cardiac myocytes (muscle).

There is a progressive accumulation of calcium in the muscle, which in turn results in increased calcium in the mitochondria. The progressive increase in mitochondrial calcium as well as the basic cardiac disease (ischemic, viral, toxic, genetic) decrease myocyte energy production and increase oxidative stress resulting in free radical damage. The combined result of these three processes promotes myocyte dysfunction and death. In addition these processes also influence skeletal muscle and contribute to fatigue and disability.

The modern pharmacological therapy of heart failure has focused on the amelioration of fluid overload and hemodynamic abnormalities and has not addressed the fundamental fact that if there is progressive loss of cardiac muscle then the patient will inevitably succumb. That is: the inexorable myocyte loss by apoptosis that occurs in heart failure is the key factor responsible for myocardial decompensation and the demise of the patients. Oxidative stress, calcium overload and cellular energy deficiency are well known as principal stimuli for the development of apoptosis.

Among the factors that aggravate myocyte dysfunction there is increasing evidence for the role of nutritional deficiencies both due to reduced intake and to insufficient intake in relation to augmented requirements caused by the underlying disease state, a phenomenon which we will refer to as "conditioned deficiency". In this situation the recommended daily allowances (RDA) do not apply, as requirements may exceed the standard RDA.

The presence of protein-energy malnutrition has been recognized by surveys of hospitalized patients using anthropometric, biochemical and immunologic measures of nutritional status. These surveys have indicated that 50–68% of patients with congestive heart failure were significantly malnourished[31]. The proportion of malnourished heart failure patients has been found to be higher than that of patients with cancer, alcoholism or those with acute infection. The cause of protein-energy malnutrition is due to both reduced intake and increased energy demands. Cardiac failure results in a cascade of metabolic effects such as tissue hypoxia, anorexia, hypermetabolism, weakness, dyspnea and hypomotility of the gastrointestinal tract all leading to poor nutrient intake. Anorexia can be aggravated by unpalatable restrictive diets or by converting enzyme inhibitors or by an excess of diuretics, opiates and digitalis. Characteristics of the disease process such as fatigue and early satiety have all been reported in congestive heart failure patients consuming self-selected diets[32,33]. These factors lead to compromised food and nutrient intake and subsequently contribute to the poor nutritional status of these cardiac patients. In addition, patients with heart failure have been shown to have significantly increased resting metabolic rates[34,35,36,37] possibly due to the increased work of breathing, fever, cytokines or elevated sympathetic nervous system outflow.

The RDA for the vitamins and related micronutrients recommended by federal nutrition authorities in Canada, the United States and Western Europe (e.g. The Canada Food Guide) are obtained through the analysis of deficiency data in otherwise healthy humans and animals. We have found that with the advent of disease, or due to genetic predisposition, specific metabolic pathways in individual organs and the function of some of these systems alter the nutritional requirements causing conditioned deficiency of both macro-(protein including amino acids, carbohydrates and fats) and micronutrients (electrolytes, trace elements, vitamins and special nutrient substances). Certain pharmaceutical agents or treatment strategies also influence these requirements.

The above considerations indicate that for heart failure and in other conditions detailed below the nutrient intake is instrumental in determining the evolution of tissue damage—its amelioration or acceleration. RDA data, although suitable for a healthy population, are not necessarily appropriate for patients suffering from certain forms of illness or predisposed to sickness through genetic constitution. There is a need for a nutritional supplement that can be taken by persons suffering from illness or with a genetic predisposition to illness.

Musculoskeletal System.

Data given above have clearly demonstrated the relationship of protein deficiency and mitochondrial dysfunction in skeletal muscle. In addition several nutrient agents have been shown to improve skeletal muscle performance. These include creatine, carnitine and taurine.

Central Nervous System.

Mitochondrial dysfunction has been noted as an important factor in several neurodegnerative diseases[38]. A central role for defective mitochondrial energy production, and the resulting increased levels of free radicals, in the pathogenesis of various neurodegenerative diseases is gaining increasing acceptance[39].

Immune System.

Immune dysfunction occurs with aging and there is growing evidence that reduced immunity is related to reduced mitochondrial dysfunctions[40].

THE INTERACTING PATHWAYS RESPONSIBLE FOR MITOCHONDRIAL FUNCTION.

We have found that the critical path in these interactions is the flow of energy substrates into the mitochondria through carnitine, the transfer of electrons through the complexes via CoQ10, and the modulation of the calcium pump by taurine. We consider the constituents of this path, namely Carnitine, CoQ10 and Taurine, to be the core constituents required to promote mitochondrial function. We have found that these compounds act together on this critical path to provide a synergistic effect.

The other constituents of the cascade given in FIG. 1 aid the action of this core by modulating oxidative stress which results from external factors and mitochondrial dysfunction and in turn promotes further dysfunction.

Adequate energy production is essential not only for cellular function but also for long term cell survival. Cellular energy production from nutrients, especially fatty acids need the coordinated action of a number of co-factors. Three factors namely, carnitine (critical for the transport of long chain fatty acid substrate), coenzyme Q10 (a key transducer for mitochondrial oxidative phosphorylation), and taurine (a key modulator of calcium accumulation) are important in promoting normal cell energetics.

DETAILS OF ALTERED MITOCHONDRIAL ENERGETICS IN HEART FAILURE.

The data for mitochondrial energetic dysfunction has been clearly documented in heart failure and therefore the following details will focus on heart failure as a paradigm.

In heart failure deficiency of carnitine promotes accumulation of toxic long-chain fatty acids; deficiency of CoQ10 alters electron transport and mitochondrial calcium accumulation also occurs, which can be corrected by the action of taurine. From FIG. 1 it can be seen that normalization of any one of the above three constituents alone will not be sufficient to significantly benefit myocardial energy production in the presence of abnormalities the other factors in the myocardial bioenergetic pathway. In addition, from FIG. 1, it can also be seen that the added action of creatine, known to be deficient in cardiac failure and antioxidants to reduce oxidative stress, known to be elevated in cardiac failure, will enhance the action of the three core constituents carnitine, CoQ10 and taurine. For these constituents to be effective in remodelling the heart, the addition of protein is essential in any supplement. These substances can be given as oral replacements to benefit both myocyte function and long-term survival. Details of the deficiencies and altered metabolism of these constituents in cardiac failure and other diseases are given below. However, it has become apparent that this paradigm applies to a number of other diseases; these will be briefly discussed in each section where appropriate.

REGULATING INTRACELLULAR CALCIUM

The failing myocardium exhibits an increase in calcium content and impaired movement of intracellular calcium. Impaired uptake of calcium adversely affects diastolic relaxation whereas the kinetics of transsarcolemmal calcium flux and calcium release by the sarcoplasmic reticulum is a principal determinant of systolic function. Chronic intracellular calcium overload ultimately leads to cell death.

Taurine:

Metabolism and Physiological Role of Myocardial Taurine.

Taurine (2-aminoethanesulfonic acid) is a unique amino acid, which lacks a carboxyl group, and as such it does not enter into protein synthesis. Taurine appears to be an important amino acid for the modulation of cellular calcium levels, exhibiting a remarkable biphasic action by increasing or decreasing calcium levels appropriate to the maintenance of cellular calcium homeostasis[41,42,43]. In the heart, taurine appears to do this by affecting several myocardial membrane systems[41,42,43]. It is reported to enhance Ca++-induced Ca++ release from the sarcoplasmic reticulum both directly and through inhibition of the enzyme phospholipid methyl transferase, influencing the phospholipid environment of the ryanodine-sensitive calcium channel. It also modulates cardiac Ca++ and Na+ through the cardiac sarcolemrnmal Na++-Ca++ exchanger and a taurine/sodium exchanger. Taurine also has antioxidant properties and reacts with a variety of potentially toxic intracellular aldehydes including acetaldehyde and malonyldialdehyde[44,45].

Taurine is found in particularly high concentrations in the heart (15–25mmole/g protein) representing approximately 60% of the free amino acid pool[41,46]. Plasma levels are approximately 50–80mmol/L. Taurine is not an essential amino acid in humans as it can be synthesized from cysteine or methionine[46]; however, most taurine in humans is obtained directly through dietary sources, particularly from fish and milk. Biosynthetic capacity is maturation dependent, being almost non-existent in the human fetus and newborn and progressively increasing until adulthood[47,48]. Taurine uptake by the myocyte is an active process and b-amino acids such as beta-alanine share the transport site; it is saturable at taurine concentrations of 200 mmole[46,48]. In the heart the transport of taurine, like that of carnitine, can be stimulated by beta-adrenergic agonists or dibutyryl-c-AMP; however, in other tissues the c-GMP pathways seem to be important[46]. The taurine transporter of all tissues is regulated by the activation of two calcium sensitive enzymes: protein kinase C (which inhibits the transporter) or calmodulin (which stimulates transport)[48]. This reciprocal regulation of intracellular taurine levels by these two enzymes is consistent with a physiologic role for taurine in the maintenance of intracellular calcium homeostasis.

The observation that TNF-α levels[49] and soluble TNF receptors[50,51] are raised in heart failure suggest increased cytokine activity in this condition. Grimble[52] has shown that the requirement for sulfur containing amino acids is increased when TNF-α is infused. Of greater significance is the fact that transsulfuration of dietary methionine to cysteine is reduced and in consequence levels of taurine and lung glutathione fall unless the animals are supplemented with cysteine. These findings suggest that with increased cytokine activity as observed by us[51] in severe heart failure, the need for cysteine and taurine will increase. Since cysteine will replenish not only taurine but also glutathione (an important endogenous antioxidant—see 'Oxidative Stress' section, below), it may be an important supplement for replenishing both.

Taurine Levels and Taurine Supplementation in Heart Failure.

Cardiac taurine concentrations are altered in heart disease. Cats have very little taurine biosynthetic capacity and may exhibit a taurine deficient cardiomyopathy[53]. Prolonged taurine depletion of the myocardium has been shown to decrease contractile force through reduction of myofibrils[54]. This finding is of interest because increased calcium levels in the myocyte can activate calcium dependant proteinases that in turn can lead to the breakdown and loss of myofibils[54]. Taurine depletion also renders the heart more susceptible to ischemic injury[55]. In this context it should be noted that myocardial taurine depletion has been reported following acute ischemic injury[56] and cardiovascular bypass surgery[57].

In species other than the cat, myocardial hypertrophy and failure is associated with an increase in cardiac taurine concentration[41,58]. In spite of this increase, orally administered taurine has been shown to have a cAMP-independent positive inotropic effect in animal models of left ventricular dysfunction[41]. Taurine administration has been shown significantly reduce calcium overload and myocardial damage in a variety of heart failure models including that induced by the calcium paradox, doxorubicin or isoproterenol or in hamster cardiomyopathy[41,59,60,61,62]; it also has been reported to increase the survival of rabbits with aortic regurgitation[63]. Taurine may have a beneficial effect on cardiac arrhythmias[64] including those associated with digitalis or catecholamine excess[65]. Studies of taurine administration in humans have been limited. However, in patients suffering from congestive heart failure taurine, given in an oral dose of 1 gram three times per day, has been reported to be extremely well tolerated and to improve both hemodynamic state and functional capacity[41,66,67].

Taurine also appears to function as an osmoregulator and neuromodulator in the brain[68]. In addition there is evidence that taurine modulates calcium influx and efflux in the brain, increases resistance to hypoxia and reduces seizure activity when administered intraperitoneally. In streptozotocin-induced diabetic rats taurine also appears to protect against the development of renal dysfunction[45]; cardiac studies have not been performed in this model. On the same lines taurine also protects the kidney and liver against doxorubicin (adriamycin) toxicity[69].

MYOCARDIAL ENERGETICS

L-Carnitine:

Carnitine in Health and Disease:

L-carnitine, an amino acid derivative (3-hydroxy-4-N-trimethylaminobutyric acid), plays a critical role in this bioenergetic pathway as it is essential for the transport of long-chain fatty acids from the cytoplasm into the sites of beta-oxidation within the mitochondrial matrix.[70] The importance of carnitine has been recognized by the observation that camitine deficiency occurs in several genetically determined metabolic abnormalities[71,72] where it is associated with the development of cardiomyopathy and skeletal muscle dysfunction. L-carnitine administration to these patients restored to a great extent cardiac and skeletal muscle function.

Evaluation of carnitine metabolism in several cardiac pathologies has led to the realization that carnitine deficiency may also be acquired and organ selective, a finding of great significance because fatty acid oxidation is a major source of energy for the myocardium. The impaired heart, regardless of the etiology of the dysfunction (including ischemic or non-ischemic dilated cardiomyopathy, coronary, hypertensive, diabetic and valvular heart disease), exhibits a marked depletion (up to 50%) of myocardial carnitine levels (particularly free carnitine) in both animal models and man[73,74,75], with evolution of the heart disease. On the other hand, despite low cardiac levels, plasma carnitine levels increase[76]. This finding makes plasma levels unrepresentative of the levels in the heart.

In addition to promoting the entry of fat into the mitochondria, carnitine binds acyl groups and releases free CoA. These processes benefit the myocyte in two ways, first it removes toxic short chain acyl groups and second maintains sufficient amounts of free CoA for mitochondrial function.

An example of the detoxifying action of carnitine is seen in the ischemic myocardium[77,78]. In ischemic myocardium or skeletal muscle there is an accumulation of long chain acyl-CoA; these compounds are potentially toxic as they exhibit both detergent-like properties and can impair mitochondrial energy production through the inhibition of a mitochondrial membrane enzyme, adenine nucleotide translocase, which transfers newly synthesized ATP from the inner mitochondria space into the cytoplasm. Carnitine protects the heart (or skeletal muscle) from the accumulation of these metabolic poisons by forming acylcamitines, which can freely diffuse out of the cell and be eliminated through the urine.

Camitine deficiency has also been observed in patients with chronic renal failure; an improvement in cardiac function following carnitine therapy has been reported for those on hemodialysis[79].

Carnitine Supplementation and Treatment:

Body stores of 1-carnitine are supplied by both diet and via endogenous biosynthesis from trimethyllysine. The concentration of carnitine in normal adult cardiac and skeletal muscle is approximately 8–15 nmol/mg non-collagen protein; plasma levels are approximately 35–50 mmol/L. Thus plasma levels are generally not good measures of tissue concentrations. Under normal conditions approximately 80% of carnitine is free and the remainder complexed as fatty acylcarnitine. A 20–50:1 intracellular to extracellular carnitine gradient is maintained by a sodium-dependent plasma membrane transport system. Camitine transport can be stimulated by beta-adrenergic agonists or dibutyryl-cAMP.

Following oral administration, peak plasma concentration occurs at 3 hours and decays with a $T_{1/2}$ of 3–4 hours; the turnover of endogenous cardiac or skeletal muscle camitine is likely on the order of several days. The bioavailability of 1-carnitine is limited to approximately 5–20% probably due to clearance by the liver. L-carnitine is well tolerated and no adverse effects have been described.

Acetyl-1-carnitine and proprionyl-1-carnitine are naturally occurring derivatives of 1-carnitine[80]. Acetyl-1-carnitine has been shown to influence mitochondrial DNA synthesis, is depleted by antiretroviral drugs and is non-toxic when infused intravenously[81]. The administration of acetyl-1-carnitine has been shown to effectively replace decreased carnitine stores in the brain and heart associated with aging in rats[82]. Acetyl-1-carnitine has excellent penetration of the CSF and is likely to be of benefit in neurodegenerative conditions such as Alzheimer's disease[81,83]. Acetyl-1-carnitine has also been shown to be of benefit to peripheral nerve function in experimental diabetes[84].

Proprionyl-1-carnitine has also been used for cardiac therapy[85,86,87,88]. Proprionyl-1-carnitine directly penetrates the cell membrane and has a high affinity for the protein carriers; within the mitochondria the enzyme carnitine acetyl transferase releases 1-carnitine and proprionyl-CoA and the latter is transformed into succinyl CoA which can prime the citric acid cycle and the production of ATP[89,90]. The proprionyl group appears to stimulate fatty acid oxidation (whereas the acetyl group inhibits this)[87].

L-carnitine (3–5 grams) or proprionyl-1-carnitine (1.5–3.0 grams) administration has been shown to result in significant hemodynamic improvement and an overall benefit in the functional capacity of animals and patients with heart failure or myocardial ischemia[72,73,79,85,86,91,92,93,94,95,96,97,98]. Clinical studies report a reduction in cadiac damage, when 1-carnitine is taken from 4–12 weeks following myocardial infarction[78,92]. It also appears to benefit patients who suffer from skeletal muscle ischemia manifested as intermittent claudication. Circulating levels of tumour necrosis factor, a cytokine that leads to muscle wasting and cardiac dysfunction, correlates with functional class and prognosis of patients with heart failure[51]; in this context it is of interest that proprionyl-1-carnitine administration tends to normalize the circulating levels of this cytokine in patients with heart failure[98].

Ubiquinone or Coenzyme Q10:

Coenzyme Q10 in Health and Disease[reviewed in 99].

Coenzyme Q10 or ubiquinone (2,3 dimethoxy-5 methyl-6-decaprenyl benzoquinone) plays a vital role as a rate-limiting carrier for the flow of electrons through complexes I, II and III of the mitochondrial respiratory chain. It is also a major endogenous lipophilic antioxidant and, like vitamin C, can regenerate a-tocopherol, the active form of vitamin E by reducing the a-tocopherol radical. A deficiency of ubiquinone caused by actual loss or through oxidation of the molecule can result in an impairment of energy production. The molecule is sited within the inner mitochondrial membrane but is also associated with the membranes of other intracellular organelles. It is also an important component of circulating LDL particles, protecting LDL from oxidation.

Ubiquinone is actively biosynthesized with the cells. The quinone ring is synthesized from the amino acid tyrosine and the polyisoprenoid side chain is formed through the acetyl CoA—mevalonate pathway. The latter pathway is under the control of the enzyme hydroxymethylglutaryl coenzyme A reductase (HMGCoA reductase) and is also used for cholesterol synthesis; inhibition of this pathway using HMG-CoA reductase inhibitors, drugs which decrease plasma cholesterol, also results in a parallel decrease in plasma ubiquinone[100] and may also reduce tissue ubiquinone levels[101].

Significantly reduced levels of myocardial ubiquinone are found in heart failure in both animal models and man[102,103,104]. Since the heart depends upon aerobic oxidation for its energy needs, ubiquinone, which is critically necessary for oxidative energy production is very important for cardiac function. The antioxidant properties of ubiquinone would add to this benefit.

Ubiquinone Supplementation and Treatment.[99,105,106,107]

Ubiquinone is widespread throughout all food groups and thus body stores may also be partially supplied by diet. The concentration of ubiquinone in normal cardiac muscle is approximately 0.4–0.5 mg/mg dry weight, slightly less in skeletal muscle and 0.6–1.3 mg/ml in plasma. Oral absorption is slow and markedly enhanced in the presence of lipid; plasma levels peak at 5–10 hours and decay with a $T_{1/2}$ of 34 hours. There is a large hepatic first pass effect so that only about 2–5% of an oral dose is taken up by the myocardium. The mean steady state level in plasma increases 4–7 fold after 4 days of dosing at 100 mg 3 times daily. Side effects are virtually absent; however, asymptomatic elevations in liver enzymes (LDH, SGOT) have been described with doses of 300 mg/day.

Oral ubiquinone therapy has been shown to result to beneficially affect cardiac dysfunction in a variety of animal paradigms[108,109,110]. Oral ubiquinone also has been reported to reduce the age-associated decline in mitochondrial respiratory function in rat skeletal muscle[111]. The controlled trials in patients with heart failure show clinical benefit, reducing symptoms, lessening hospitalization and improving myocardial performance[99,,102,103,105,112,113,114,115].

Creatine:
Role of Creatine in Health and Disease.

Creatine phosphate (PCr) is the primary high-energy phosphate reservoir of the heart and skeletal muscle. High-energy phosphate is transferred from PCr to ADP to form ATP through catalysis by creatine kinase[116]:

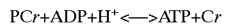

$$PCr + ADP + H^+ \longleftrightarrow ATP + Cr$$

Muscle creatine stores are maintained through biosynthesis from endogenous precursors arginine, glycine, and methionine in the liver, pancreas and kidneys, and through the ingestion of meat and fish. The concentration of total creatine in normal adult human myocardium or skeletal muscle is approximately 140 mmol/g protein; creatine phosphate constitutes about 65–80% of the total creatine under aerobic conditions[116]. Creatine is accumulated by muscle against a large concentration gradient from the blood; the transporter is probably driven by the extracellular/intracellular Na electrochemical potential [116,,117]. There is evidence that increased adrenergic drive (a characteristic of heart failure) can decrease myocardial creatine and creatine kinase stores[123,124].

Experimental creatine depletion in animals results in structural, metabolic and functional abnormalities in muscle[117]. Myocardial creatine content and myocardial energetics is reduced in a wide variety of animal paradigms of heart failure[116,118,119,123,120]. No data is available regarding creatine replacement in these models. However creatine has been shown to attenuate myocardial metabolic stress in rats caused by inhibition of nitric oxide synthesis[121].

Hearts from patients with coronary artery disease, aortic stenosis or heart failure all show a marked reduction in total creatine (up to 50%) with an expected concomitant reduction in creatine phosphate[122,123]; creatine kinase is also reduced[116,117]. These reductions interact synergistically decreasing myocardial capacity for ATP synthesis by up to 80%[116,117,124]. Such an energy deficit has a significantly adverse impact on myocardial function and survival. Similar abnormalities of energy stores and production are seen in the skeletal muscles of patients of heart failure; these play an important role in compromising the functional capacity of these patients[125]. Recently, it has been reported that the myocardial PCr/ ATP ratio may be a better predictor of patient mortality in dilated cardiomyopathy than left ventricular ejection fraction or the patients functional class[126].

Creatine Supplementation and Treatment.

The role of creatine supplementation may not be observed in normal cardiac or skeletal muscle under normal levels of performance. However, supplementation has been shown to increase performance in situations where the availability of creatine phosphate is important[127,128]. Ingestion of 3 g of creatine per day for one month (or 20 g per day for one week) increases muscle creatine content and can improve performance[129]. Daily turnover of creatine to creatinine for a 70 kg male has been estimated to be approximately 2 g[99]. Creatine supplements will increase skeletal muscle creatine and increase muscle resistance to fatigue during short-term intense exercise where it reduces lactate accumulation[130,131,132]. It also appears to be of benefit when given in adequate doses to patients with heart failure where myocardial and perhaps skeletal muscle creatine and creatine phosphate levels are depressed. The administration of a creatine supplement to patients with heart failure did not increase cardiac ejection fraction but significantly increased not only skeletal muscle creatine phosphate but also muscle strength and endurance[133] and thus would benefit patient symptom-limited performance.

Thiamine:

Thiamine or vitamin B. status may be compromised in heart failure due to a variety of causes. Thiamine is a water-soluble vitamin which fimctions as a coenzyme in a variety of enzyme systems especially those related to energy metabolism. Thiamine is stored in very small quantities (approximately 30 mg) with approximately half of the body stores being found in skeletal muscle with the remainder being found in the heart, kidney and nervous tissue including the brain. Since little is stored, thiamine requirements must be met daily. Thiamine requirements are related to daily energy expenditure[134] and metabolizable energy intake, especially carbohydrate intake and therefore patients with increased metabolic rates or poor intakes, such as those with heart failure, may be at increased risk for deficiency during acute illness[134,135]. The Food and Nutrition Board, USA recommends that for adults with energy intakes below 2000 kcal/day that a basal requirement of 1.0 mg thiamine per day be maintained[136]. The Canadian recommendations support an intake of 0.4 mg/1000 kcal or no less than 0.8 mg/day for adults[137]. Thiamine intake in patients with heart disease has been examined in only one study using a semi-quantitative food frequency questionnaire focusing on foods high in thiamine[138]. Nutrient analysis indicated a low overall intake of thiamine of 0.966 mg/day with 33% of patients not meeting the Recommended Dietary Allowance (RDA) for thiamine[65]. This study also indicated that thiamine-deficient diets were more common among patients treated as out-patients rather than in-patients.

Necropsy studies indicate that thiamine deficiency is underdiagnosed in life[135]. Classical deficiency signs are often absent or they are not recognized[139]. Thiamine deficiency results in beri beri, which can have neurological or cardiac effects. The symptoms that are most common are mental confusion, anorexia, muscle weakness ataxia, edema, muscle wasting, tachycardia and an enlarged heart[140]. Thiamine deficiency leads to several major derangements of the cardiovascular system including peripheral dilatation leading to a high output state, biventricular myocardial failure, retention of sodium and water leading to edema as well as a relative depression of left ventricular function with low ejection fraction[140,141]. This picture will be masked in preexisting low-output heart failure. Since thiamine deficiency will exacerbate co-existing heart failure, correction of this deficiency through supplementation has the potential to improve cardiac status in patients with congestive heart failure.

In addition to poor dietary intake and increased metabolic utilization, referred to above, patients with heart failure also may be at risk for thiamine deficiency because of their need for diuretics. There is evidence from both animal and human studies that diuretics, especially those which affect the Loop of Henle such as furosemide, cause increased urinary losses of thiamine even in the presence of thiamine deficiency[142,143]. It appears that furosemide treatment may block the kidneys ability to adapt thiamine excretion in order to prevent thiamine deficiency. These data demonstrate that patients with heart failure are at increased risk of thiamine deficiency due to a combination of 1) poor intake resulting from anorexia and unpalatable diets, 2) hypermetabolism, and 3) enhanced excretion caused by the concurrent use of diuretics.

There have been a handful of studies which support a high prevalence of thiamine deficiency in both in-and outpatients with congestive heart failure—from 13% to 91% depending on the population studied[138,143,144,145]. A very high (91%) prevalence of thiamine deficiency has been reported in a group of congestive heart patients on long-term furosemide treatment[143]. The average dose of furosemide ranged from 80–240 mg/day. Biochemically, the furosemide-treated group had severe thiamine deficiency indicating that doses of this magnitude have significant effects on thiamine status. These investigators undertook a randomized double-blind trial of thiamine supplementation in 30 in-patients with heart failure and on long-term furosemide therapy[146]. Patients were randomized to receive 200 mg intravenous thiamine or a placebo for seven days after which all subjects were placed on an oral supplement of 200 mg/day of thiamine and followed for an additional six weeks. They saw a significant diuresis with increased excretion of sodium and water within two days of thiamine supplementation in comparison with the placebo group whose excretion remained constant. The mean left ventricular ejection fraction increased significantly after one week of thiamine supplementation but not with the placebo. After six weeks of oral thiamine supplementation left ventricular ejection fraction was increased by 22%. This study demonstrates a significant improvement in left ventricular function as a result of thiamine supplementation in patients with CHF. In addition, improvement in left ventricular function was accompanied by diuresis and increased sodium excretion, which is hypothesized to be one of the major effects of thiamine supplementation. Finally, it should also be noted that thiamine deficiency is also commonly present in patients on hemodialysis[147], in patients in intensive care units[148] and perhaps cognitive impairment in the aged[149].

REDUCING OXIDATIVE STRESS

Cells are constantly subjected to interplay between free radical injury and protective mechanisms to prevent or minimize free radical injury. Oxidative stress has been defined as a disturbance in the equilibrium between pro-and anti-oxidative systems. A number of different challenges increase oxidative stress resulting in damage to lipids, proteins, DNA and carbohydrates. Dietary Antioxidants—Vitamin E, Vitamin C, Cysteine and Selenium—counteract the effect of free radicals generated by external factors and by mitochondrial dysfunction. Cysteine is the precursor of glutathione, one of the most potent antioxidants present in the cell.

Role of Oxidative Stress in Cardiac Disease.

Until recently there has been a reluctance to accept that oxidative stress can be important in the pathogenesis of cardiac disease however, recent investigation suggests that oxidative stress may be a very important contributor to the deterioration of the hypertrophied or failing myocardium. For example, reactive oxygen species have been shown to be critical components of the apoptosis pathway[150]; myocyte loss by apoptosis is now thought to be a significant contributor to the inexorable deterioration of the failing myocardium[151]. The importance of oxidative stress in heart failure is not surprising because a number of factors associated with heart failure, such as increased plasma catecholamines,[152] and cardiac sympathetic tonel[153], microvascular reperfusion injury[154,155] cytokine stimulation[49,50] and mitochondrial DNA mutations (particularly complex I)[156] are known stimuli for free radical production and oxidative stress[157,158,159,160]. Coenzyme Q10 and taurine (and its precursor cysteine), discussed above are important endogenous antioxidants or antioxidant precursors.

Peroxidative damage has been demonstrated in the hearts of dogs, guinea pigs and rats with heart failure due to pressure or volume overload[161,162,163]. Vitamin E administration benefited[164] both myocardial structure and function. We have observed decreases in the levels of glutathione peroxidase and a-tocopherol and a concomitant increase in protein oxidation in the myocardium of cardiomyopathic hamsters during the late stages of hamster cardiomyopathy[165]; an elevation of myocardial free radicals and lipid peroxides have also been demonstrated in this model[166]. The administration of vitamin E appears to completely normalize these findings[163].

Recently, we have also demonstrated a significant increase in the plasma level of lipid peroxides and malonyldialdehyde, markers of oxidative stress, in patients suffering from congestive heart failure[51]. The increase in oxidative stress was related to the clinical severity of heart failure with the highest levels of lipid peroxidation and malonyldialdehyde being observed in class 3 and class 4 patients. Increased free radical activity is also seen in patients on life support or in intensive care unit settings[167]. These observations suggest that antioxidant supplements should be important additions to the therapy of heart failure and severely ill patients.

The ability to withstand peroxidative injury is partially dependent on diet. A good dietary intake of the antioxidant vitamins C and E, and trace nutrient minerals such as selenium together with adequate cysteine as a precursor for glutathione synthesis are important for protection against free radical injury. Fat intake and composition is also important, the need for vitamin E may be increased by an increased intake of polyunsaturated fatty acids[168]. It has been suggested that the vitamin E requirement=5.96+0.25 (% PUFA kcal+g PUFAs). With the North American diet increasing in PUFA, Diplock has suggested that the current RDA (recommended daily allowances) be increased four-fold[169]. Dietary antioxidants may reduce the risk of ischemic heart disease and the extent of myocardial infarction[170,171,172]. Recent reports suggest an increased need for vitamin C in patients with diabetes mellitus[173]. Finally oxidative stress is also felt to be a major contributor to chronic neurodegenerative disease and the tissue deterioration and immune dysfunction associated with aging[174,175,176,177,178,179,180,181,182,183,184].

Correction of Mitochondrial Abnormalities.

Other investigators have used certain of these nutrients alone. We have found that a preferred nutritional supplement would replace the constituents given above and influence several metabolic pathways interacting to subserve mitochondrial function. We have found that replacing only one of the core constituents will not correct the connected abnormalities in multiple parts of the myocardial bioenergetic pathway which is deranged in cardiac failure. Rather, our supplement helps to correct the cascading series of metabolic abnormalities in patients with myocardial dysfunction and other diseases mentioned above, rather than merely a problem at a single point in a pathway.

BRIEF SUMMARY OF THE INVENTION

Figure 1:
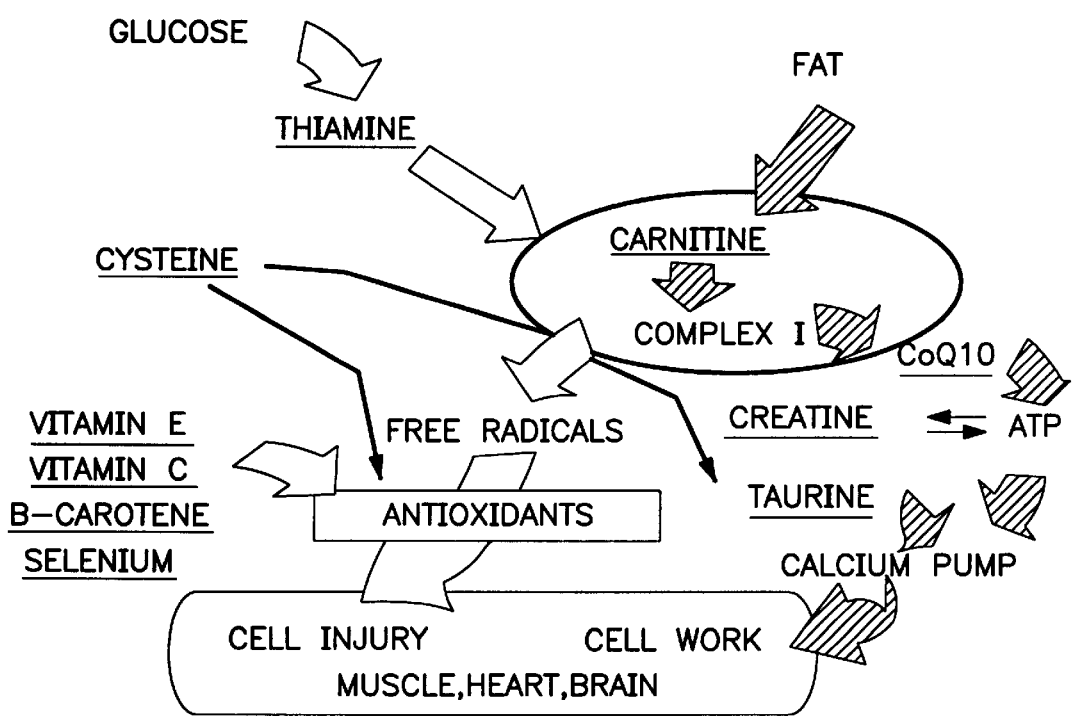
FIG. 1 is a schematic diagram of the interaction of the nutrients included in this invention and their interaction in cell energetics.

Researchers have not recognized that optimizing mitochondrial function depends upon the synergistic correction of cellular and mitochondrial energy substrates (FIG. 1) which will lead to improved energetics, reduced oxidative stress and better calcium homeostasis, a synergistic response clinically beneficial to the patient.

The conventional approach has been to try single nutrients. This has led to conflicting results, at best.

The combination of nutrients of this invention addresses what we have found to be an interrelated series of disruptions in cellular metabolism, that are present in heart failure and conditions such as aging, chronic neurodegenerative disease, immune diseases such as AIDS, chronic multisystem disease, chronic lung or renal disease, chronic fatigue syndrome, patients on immunosuppressive drugs post-transplantation, cancer patients on doxorubicin or related drugs, wasting or cachexia from cancer or sepsis and in normal humans wishing better neuromuscular or athletic performance, and thus provides more reliable, effective treatment.

The combination is preferably delivered orally, but other methods of administration such as intravenous administration may be used.

The invention is a nutritional supplement that helps to correct or prevent the cascading series of metabolic abnormalities responsible principally for cardiac disease but will have a similar effect on neuromuscular, central nervous and immune system dysfunction in a wide variety of diseases.

Rather than merely addressing problems at particular points in metabolic pathways, the nutritional supplement of the invention uses a holistic approach to restoring and improving function at many points in cell metabolism, for example at multiple points along the mitochondrial bioenergetic pathway. The effectiveness of this nutritional supplement in preventing and correcting myocardial dysfunction has been demonstrated in vivo (Example 1). This invention relates to a dietary supplement comprising effective amounts of L-Carnitine (or its functional analogues such as Acetyl-Carnitine or Proprionyl-1-Carnitine), Coenzyme Q10 (Ubiquinone or its functional analogues) and Taurine as the minimal number of core constituents essential for the correction of the abnormality in mitochondrial energetics in cardiac failure and the different diseases referred to above. Additional supplementation with Cysteine, Creatine, Vitamin E (RRR-d-alpha-tocopheryl), Vitamin C (ascorbic acid), Selenium, and Thiamin in a high protein nutritional feeding are preferred.

In a preferred embodiment this invention relates to a dietary supplement taken in a high protein formulation such as a dairy based drink, a dehydrated dairy product, soya based drink or dehydrated product, or a nutritional bar containing: L-Carnitine 0.5–5 g or its functional analogues such as Acetyl- and Proprionyl-1-Carnitine 3 g, Coenzyme Q10 (Ubiquinone) 30–200 mg or its functional analogues, Taurine 0.1–3 g. Addition of Cysteine 0.5gm–1.5 g, Creatine 2.5 g, Vitamin E (RRR-d-alpha-tocopheryl) 600 IU, Vitamin C (ascorbic acid) 1000 mg, Selenium 50 mcg, Thiamine 25 mg will aid the action of the core constituents. These doses may vary 25% to 300% for specialized formulations.

This formulation ensures a high quality protein to optimize muscle function so as to allow the above nutrients in combination to synergistically interact for the benefit of the patient—that is the effect of all of the ingredients combined will be greater than the sum of the individual parts as they address a cascading series of metabolic abnormalities. There is a core of specific nutrients, which must be combined to be effective, and a larger number for optimal effectiveness. Conversely omission of the core will detract from the overall efficacy of this supplement. In addition to maintaining protein stores, the supplement corrects abnormalities in: (a) myocardial energetics, (b) intracellular calcium and (c) oxidative stress.

This supplement also benefits patients, with or without heart failure, with other conditions in which cellular nutrition, mitochondrial energetics and function are impaired or less than desired and oxidative stress is increased, including but not exclusively for musculoskeletal, immune and disorders of the central nervous system especially those related to aging. Such disorders include neurodegenerative disease, immune diseases, stroke, AIDS, chronic multisystem disease, respiratory muscle fatigue such as chronic obstructive lung disease, lung or renal disease, chronic fatigue syndrome, patients on immunosuppressive drugs, cancer patients treated with drugs such as doxorubicin, wasting, cachexia from cancer or sepsis Effectiveness of Nutrient Cocktail In Vivo:

In vivo data gained from cardiomyopathic hamsters showed the synergistic effect of the nutritional supplement (Experiment 1). It also showed the feasibility of providing a cocktail of nutrients to cardiomyopathic hamsters and that the mixture positively affected cardiac structure, function and markers of oxidative stress, deterioration of mitochondrial and myofibrillar structures in non-treated animals with improved preservation in treated animals. The results show that there are increased areas of necrosis in non-treated hearts in comparison with treated hearts. These results show that this cocktail of nutrients is effective in preserving myocyte function and structure.

Example 1—Cardiac Nutrient Cocktail Study

We performed a pilot study in order to determine the feasibility of providing a "cocktail" of nutrients as well as their effect on indices of oxidative stress as well as on myocardial structure and function.

| Composition of Cardiac Cocktail | |
| --- | --- |
| L-carnitine | 300 mg/kg/day |
| Vitamin E | 147 mg/kg/day |
| Vitamin C | 100 mg/kg/day |
| Coenzyme $Q_{10}$ | 15 mg/kg/day |
| Thiamine ($B_1$) | 100 mg/kg |
| Cysteine | 12 mg/day |
| Selenium | 0.05 mg/day (5 mg/kg diet) |
| Taurine | 188 mg/day (18.8 g/L) |
| Creatine | 100 mg/day (1% diet) |

Method of Delivery

The nutrients were delivered in 10 of raspberry Jell-O. Water soluble nutrients were added directly to the cooled Jell-O while lipid soluble components were mixed with 15 ml 20% intralipid prior to the in addition to the cocktail mixture.

Study Design 180-day old cardiomyopathic hamsters were started on supplementation after a two-week acclimation period. 18 animals received Jell-O supplemented with nutrients while 18 received the identical Jell-O but without nutrients. The animals received full supplementation for eight weeks, at this time the animals were 278 days of age. At this time, 6 treated, 6 untreated and 6 non-diseased hamsters underwent the Langendorff procedure modified for hamsters following which the hearts were preserved for electron microscopy. The remaining animals were sacrificed and blood, hearts, livers and muscle were collected for biochemistry.

Results a) Mortality—In the treated group, 2 hamsters died. Of the non-treated group, 4 hamsters died with an additional hamster being moribund at the time of study.

b) Appearance—The treated hamsters remained active and alert with no visible edema. In contrast, two of the non-treated animals became grossly edematous with exceptionally large black livers. The control non-treated animals were less active and appeared less bright.

c) Biochemistry—The heart and plasma were analysed for indices of oxidative stress.

| | Control-Non Treated | Cocktail Treated | |
| --- | --- | --- | --- |
| Heart Glutathione Peroxidase Activity Units/min/mg protein | 113.05 ± 8.20 | 134.34 ± 16.7 | |
| Heart Malondialydehyde ug/g wet weight | 2.00 ± 0.25 | 1.67 ± 0.22 | |
| Plasma Malondialydehyde nmol/ml plasma | 0.17 ± 0.009 | 0.14 ± 0.04 | |
| Plasma Glutathione Peroxidase Activity Units/min/mg protein | 5.24 ± 0.82 | 6.03 ± 0.51 | |
| Ratio Heart Weight:Body Weight | 0.008 ± 0.0007 | 0.007 ± 0.0006 | |
| D. Function | Non-Treated | Treated | Normal Hamster |
| * Mean Pressure-Langendorff mmHg | 20.84 ± 5.97 | 44.17 ± 4.55 | 92.50 ± 11.99 |

Figure 2A:
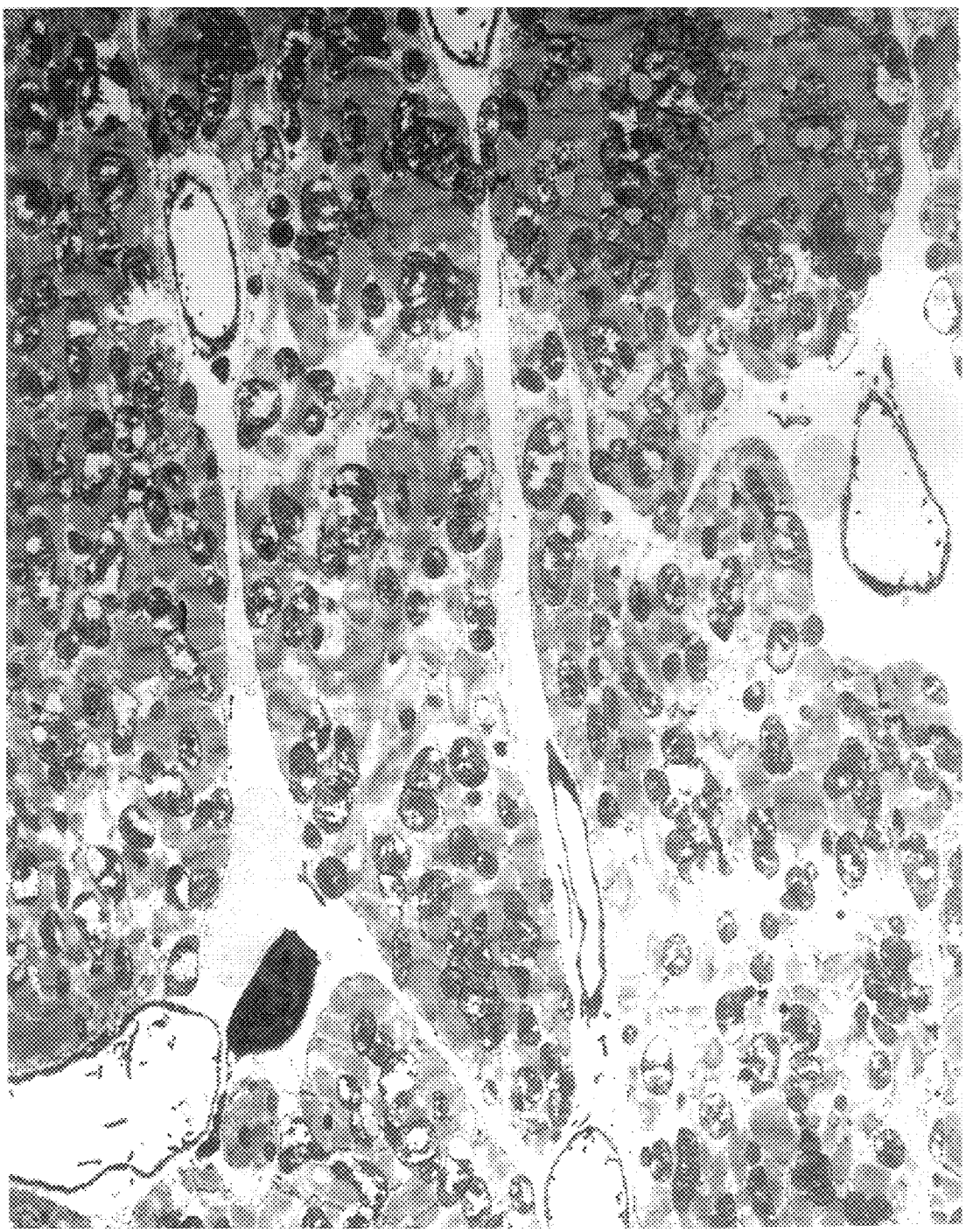
FIG. 2 shows electron micrographs of heart specimens from hamsters in Experiment 1. (a) control non-treated heart (b) cocktail treated heart (c) normal hamster heart.
Figure 2B:
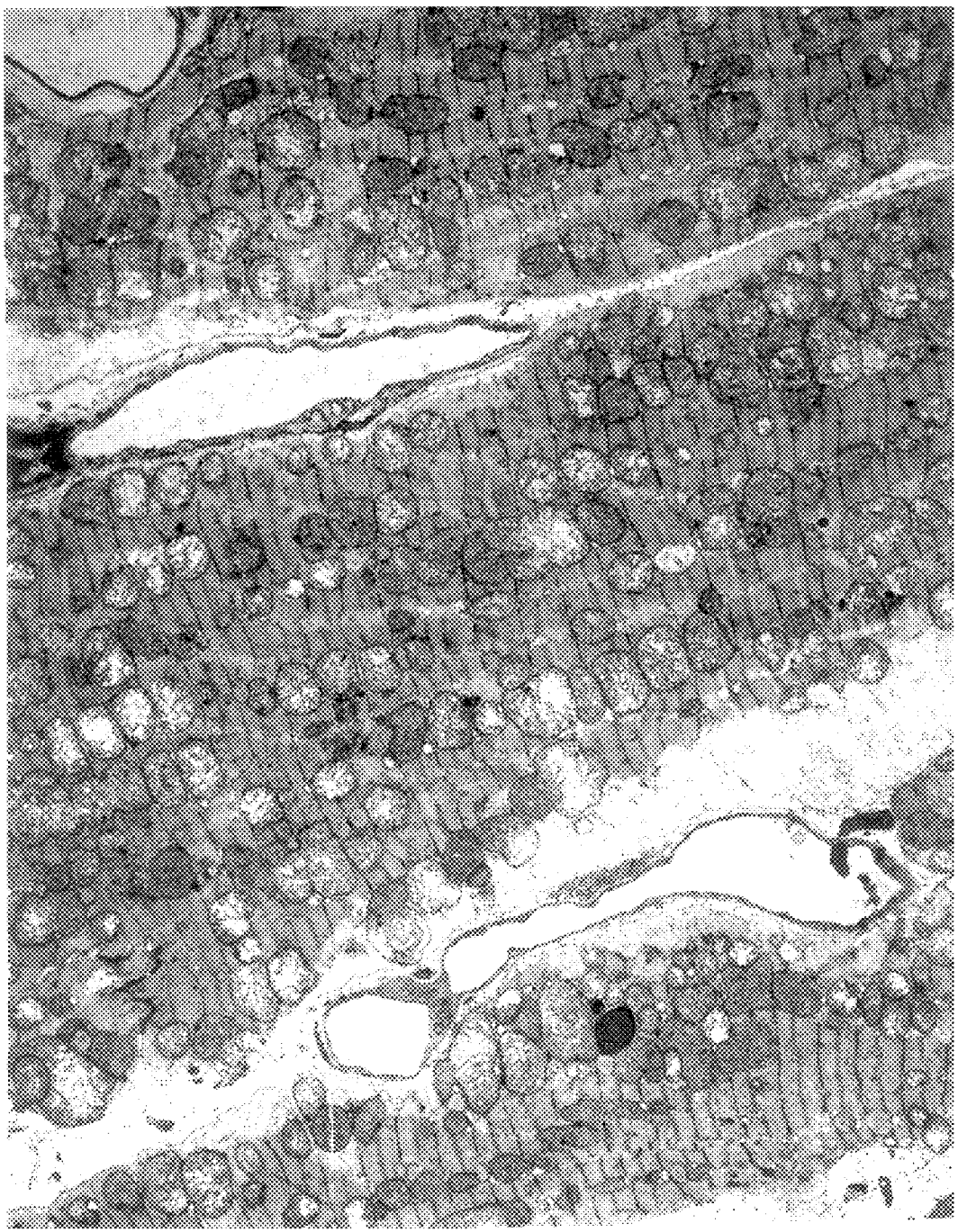
Figure 2C:
Figure 3A:
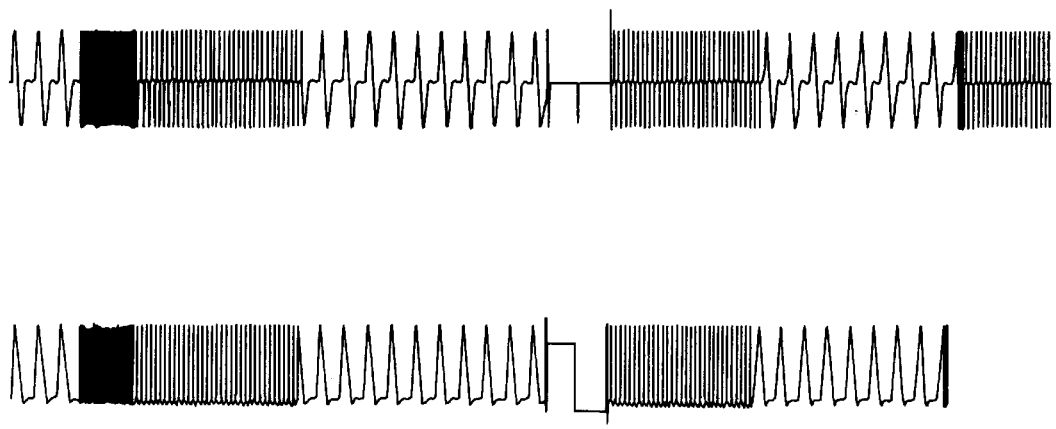
FIG. 3 shows the mean pressure of contraction of hamster hearts (Langendorff Model) in Experiment 1. (a) normal hamster heart (b) control non-treated heart (c) control non treated heart (d) control non-treated heart and cocktail treated heart (e) cocktail treated heart (f) cocktail treated heart.
Figure 3B:
Figure 3B:
Figure 3C:
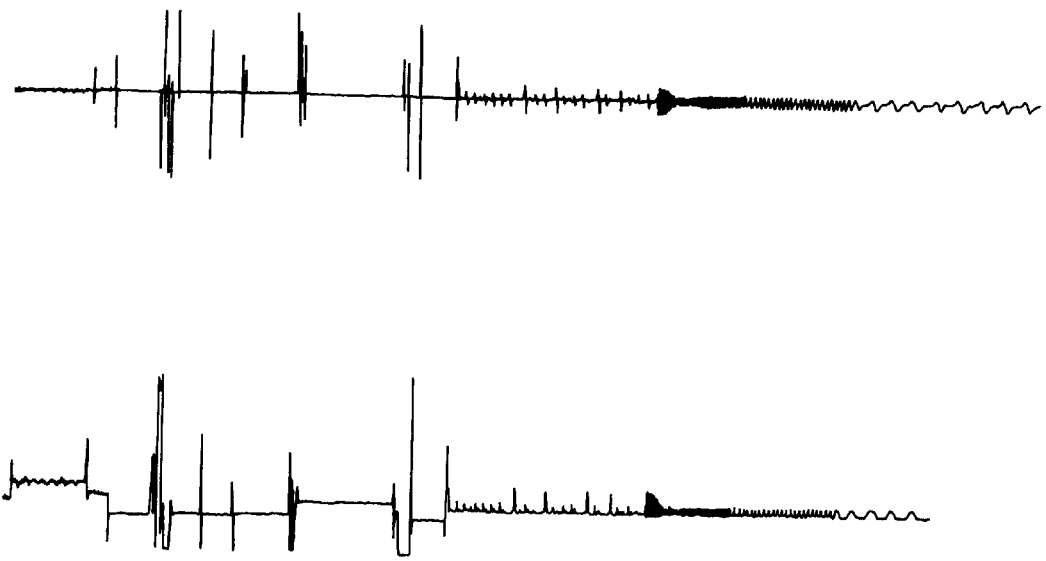
Figure 3D:
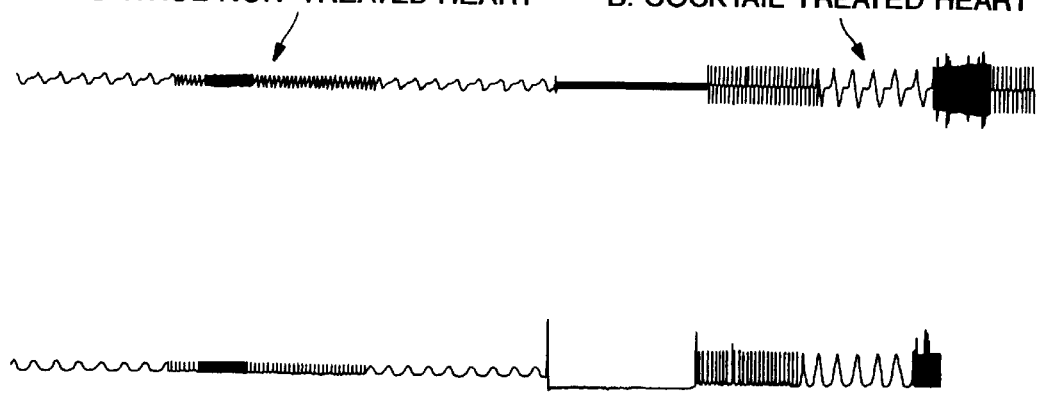
Figure 3E:
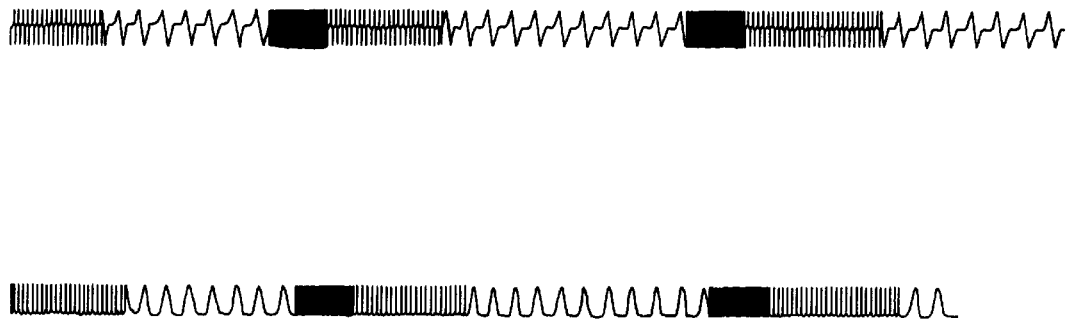
Figure 3F:
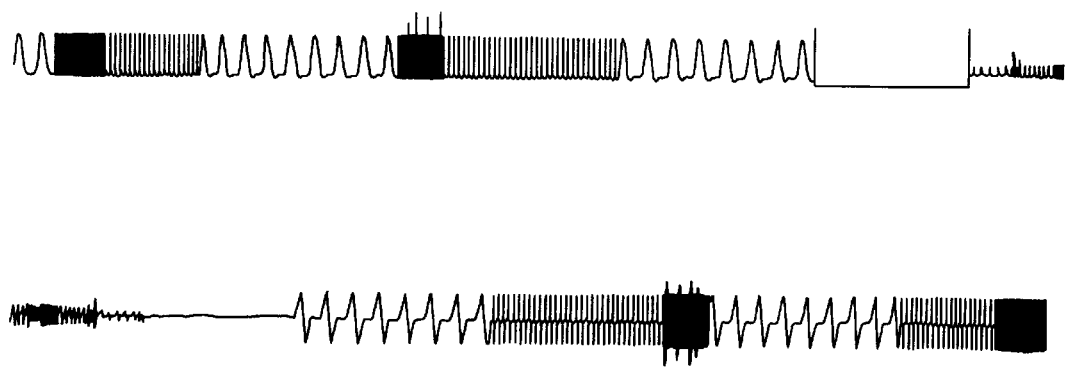

* See attached tracings (FIGS. 3(a)–(f))

d) Microscopy—Electron micrographs (FIGS. 2 (a)–c)) show deterioration of mitochondrial and myofibrillar structures in non-treated animals with markedly improved preservation in treated animals. In addition, there are increased areas of necrosis in non-treated hearts in comparison with treated hearts. The results achieved were superior to those projected not shown from individual studies of the ingredients.

e) Recently we have completed another study with the supplement and confirmed all the above results and in addition have shown a complete restoration of systolic contractility as measured by +dP/dT and diastolic relaxation as measured by −dP/dT.

Conclusions

Nutrients have been used, singly or in random combination to treat several conditions including heart disease. We by contrast have found that three defined key components, L-carnitine, coenzyme Q10 and taurine, interact in a way which potentiates the action of each on cell function and energetics. Creatine, thiamine and antioxidants support the action of this core. In addition protein enrichment also aids the maintenance of mitochondrial energetics. We have demonstrated the validity of this claim by preventing the development of heart failure in a genetic animal model normally subject to the inexorable progression of heart failure culminating in death. Other studies using nutrients have not shown comparable benefit.

All publications, patents and patent applications are herein incorporated by reference in their entirety to the same extent as if each individual publication, patent or patent application was specifically and individually indicated to be incorporated by reference in its entirety.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

We claim:

1. A nutritional supplement comprising at least about 3 g of L-Carnitine or its functional analogue, at least about 150 mg of Coenzyme Q10 (Ubiquinone) or its functional analogue and at least about 3 g of Taurine or its precursors.

2. A nutritional supplement comprising at least about 3 g of L-Carnitine, at least about 150 mg of Coenzyme Q10 (Ubiquinone) and at least about 3 g of Taurine.

3. The nutritional supplement of claim 1, consisting essentially of at least about 3 g of L-Carmitine or its functional analogue, at least about 150 mg of Coenzyme Q10 (Ubiquinone) or its functional analogue and at least about 3 g of Taurine or its precursors.

4. The nutritional supplement of claim 2, consisting essentially of at least about 3 g of L-Carnitine, at least about 150 mg of Coenzyme Q10 (Ubiquinone) and at least about 3 g of Taurine.

5. The nutritional supplement of any one of claims 1, 2, 3, or 4, comprising at least about 200 mg of Coenzyme Q10 (Ubiquinone) or its functional analogue.

6. The nutritional supplement of claim 3 or claim 4, further comprising a carrier.

7. The nutritional supplement of claim 6, wherein the carrier comprises a water-lipid emulsion.

8. The nutritional supplement of claim 7, wherein the water-lipid emulsion comprises a protein-lipid emulsion.

9. The nutritional supplement of claim 8, wherein the protein-lipid emulsion comprises a bar.

10. The nutritional supplement of claim 8, wherein the wherein the protein-lipid emulsion is selected from the group consisting of a liquid dairy based product, a dehydrated dairy based product, and a soy based product.

11. The nutritional supplement of any one of claims 1, 2, 3, or 4, further comprising a compound selected from the group consisting of Cysteine, Creatine, Vitamin E, Vitamin C (ascorbic acid), Selenium, and Thiamine.

12. A method of medical treatment of a disease, disorder or abnormal physical state selected from the group consisting of heart disease, functional deterioration associated with ageing, neurodegenerative disease, immune disease, stroke, AIDS, chronic multisystem disease, respiratory muscle fatigue, chronic obstructive lung disease, lung disease, renal disease, chronic fatigue syndrome, effects of immunosuppressive drugs on patients, effects of chemotherapy drugs on cancer patients, wasting, cachexia and a disease, disorder or abnormal physical state including impaired cellular nutrition and mitochondrial energetics and increased oxidative stress, the method comprising administering to a human an effective amount of a carrier and a nutritional supplement comprising L-Camnitine or its functional analogue, Coenzyme Q10 (Ubiquinone) or its functional analogue and Taurine or its precursors in a single or divided daily dose.

13. A method of medical treatment of a disease, disorder or abnormal physical state selected from the group consisting of heart disease, functional deterioration associated with ageing, neurodegenerative disease, immune disease, stroke, AIDS, chronic multisystem disease, respiratory muscle fatigue, chronic obstructive lung disease, lung disease, renal disease, chronic fatigue syndrome, effects of immunosuppressive drugs on patients, effects of chemotherapy drugs on cancer patients, wasting, cachexia and a disease, disorder or abnormal physical state including impaired cellular nutrition and mitochondrial energetics and increased oxidative stress, the method comprising administering to a human an effective amount of a carrier and a nutritional supplement comprising L-Carnitine, Coenzyme Q10 (Ubiquinone) and Taurine or its precursors in a single or divided daily dose.

14. The method of claim 12, comprising administering to a human a carrier and a nutritional supplement comprising at least about 3 g of L-Carnitine or its functional analogue, at least about 150 mg of Coenzyme Q10 (Ubiquinone) or its functional analogue and at least about 3 g of Taurine or its precursors in a single or divided daily dose.

15. The method of claim 13 comprising administering to a human a carrier and a nutritional supplement comprising at least about 3 g of L-Carnitine, at least about 150 mg of Coenzyme Q10 (Ubiquinone) and at least about 3 g of Taurine in a single or divided daily dose.

16. The method of claim 14, comprising administering to a human a carrier and a nutritional supplement consisting essentially of at least about 3 g of L-Carnitine or its functional analogue, at least about 150 mg of Coenzyme Q10 (Ubiquinone) or its functional analogue and at least about 3 g of Taurine or its precursors in a single or divided daily dose.

17. The method of claim 15, comprising administering to a human a carrier and a nutritional supplement consisting essentially of at least about 3 g of L-Carnitine, at least about 150 mg of Coenzyme Q10 (Ubiquinone) and at least about 3 g of Taurine in a single or divided daily dose.

18. The method of claim 14 or 16, wherein the nutritional supplement comprises at least about 200 mg of Coenzyme Q10 (Ubiquinone) or its functional analogue.

19. The method of any one of claims 14, 15, 16 or 17, wherein the nutritional supplement comprises at least about 200 mg of Coenzyme Q10 (Ubiquinone).

20. The method of any one of claims 12, 13, 14, 15, 16 or 17, the nutritional supplement further comprising at least one compound selected from the group consisting of Cysteine, Creatine, Vitamin E, Vitamin C (ascorbic acid); Selenium, and Thiamine.

21. The method of any one of claims 12, 13, 14, 15, 16 or 17, wherein the carrier comprises a water-lipid emulsion.

22. The method of any one of claims 12, 13, 14, 15, 16 or 17, wherein the carrier comprises a protein formulation.

23. The method of claim 22, wherein the protein formulation comprises a bar.

24. The method of claim 22, wherein the wherein the protein formulation is selected from the group consisting of a liquid dairy based product, a dehydrated dairy based product, and a soy based product.

25. The method of any one of claims 12, 13, 14, 15, 16 or 17, wherein the disease comprises heart disease.

* * * * *